(12) United States Patent
Stankard et al.

(10) Patent No.: US 10,117,638 B2
(45) Date of Patent: Nov. 6, 2018

(54) ULTRASOUND SYSTEM AND APPARATUS HAVING A PORTABLE STORAGE BIN

(71) Applicant: GENERAL ELECTRIC COMPANY, Schenectady, NY (US)

(72) Inventors: Philip Stankard, Mcfarland, WI (US); Robert Andrew Meurer, Waukesha, WI (US); Muriel Shields, Wimberley, TX (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 68 days.

(21) Appl. No.: 15/353,869

(22) Filed: Nov. 17, 2016

(65) Prior Publication Data
US 2018/0132822 A1 May 17, 2018

(51) Int. Cl.
*A61B 8/00* (2006.01)
*H05K 5/00* (2006.01)
*H05K 7/00* (2006.01)

(52) U.S. Cl.
CPC .......... *A61B 8/4405* (2013.01); *A61B 8/4433* (2013.01); *A61B 8/462* (2013.01); *H05K 5/00* (2013.01); *H05K 7/00* (2013.01); *A61B 8/00* (2013.01)

(58) Field of Classification Search
None
See application file for complete search history.

(56) References Cited

U.S. PATENT DOCUMENTS

| 5,615,678 A | 4/1997 | Kirkham et al. |
| 6,471,634 B1 | 10/2002 | Dykes et al. |
| 6,640,159 B2* | 10/2003 | Holmes ............... G07F 17/0092 700/236 |
| 6,663,569 B1 | 12/2003 | Wilkins et al. |
| 6,980,419 B2 | 12/2005 | Smith et al. |
| 2009/0247877 A1* | 10/2009 | Tanaka ..................... A61B 8/12 600/462 |
| 2009/0275892 A1* | 11/2009 | Molnar ................ A61B 8/4218 604/116 |
| 2011/0201927 A1 | 8/2011 | Hayakawa et al. |
| 2011/0315648 A1* | 12/2011 | Buttigieg ............. A47B 49/004 211/163 |
| 2012/0323362 A1* | 12/2012 | Paydar ................ G06F 19/3462 700/237 |
| 2015/0011872 A1* | 1/2015 | Koh ...................... A61B 5/4887 600/424 |
| 2015/0091422 A1* | 4/2015 | Adler ................... A61G 12/001 312/249.12 |

* cited by examiner

*Primary Examiner* — Dimary Lopez Cruz
*Assistant Examiner* — Zhengfu Feng
(74) *Attorney, Agent, or Firm* — Grogan, Tuccillo & Vanderleeden LLP

(57) ABSTRACT

An ultrasound apparatus includes a base, a housing extending upwardly from the base and having opposed lateral sides, the housing being configured to support an operator console and display, and a storage bin received in a recess in the housing. The storage bin is movable from a first position in which the storage bin is received within the recess of the housing, and a second position in which the storage bin extends from one of the lateral sides of the housing.

16 Claims, 10 Drawing Sheets

ULTRASOUND SYSTEM AND APPARATUS HAVING A PORTABLE STORAGE BIN

BACKGROUND

Technical Field

Embodiments of the invention relate generally to medical imaging systems and, more particularly, to an ultrasound system and apparatus having a portable storage bin.

Discussion of Art

An ultrasound imaging system typically includes an ultrasound probe that is applied to a patient's body and a processor and display device that is operably coupled to the probe. The probe may be controlled by an operator of the system and is configured to transmit and receive ultrasound signals that are processed into an ultrasound image by the processor and shown on the display device. During an imaging session, the operator typically views an imaging screen associated with the display device, which includes the ultrasound image, and controls the probe and the image displayed through an operator interface.

Many ultrasound imaging systems and other medial imaging devices may be mounted or integrated into a wheeled cart that provides for portability, enabling technicians to move the system from room to room and patient to patient. With any such portable medical imaging systems, and ultrasound imaging systems in particular, there is always a need for storage space to contain and keep near at hand the numerous items needed to properly carry out the imaging process. Due to the limited space in most clinical settings and hospitals, it is most convenient to provide the imaging system with a close at hand storage facility that is easy to access and which can have sufficient space to contain the necessary accessories ready for the technician. While existing systems may include various recesses and small bins for holding some accessories, they are often not large enough to accommodate everything that may be needed during typical system use, which can include cleaning wipes, gel for the probe, towels, biopsy kits and other odds and ends.

In view of the above, there is a need for a medical imaging system and, in particular, an ultrasound system that has a portable storage bin for storing equipment and supplies needed for system operation which is easily accessible when needed and can be moved and stowed out of the way when not being used.

BRIEF DESCRIPTION

In an embodiment, an ultrasound apparatus is provided. The ultrasound apparatus includes a base, a housing extending upwardly from the base and having opposed lateral sides, the housing being configured to support an operator console and display, and a storage bin received in a recess in the housing. The storage bin is movable from a first position in which the storage bin is received within the recess of the housing, and a second position in which the storage bin extends from one of the lateral sides of the housing.

In another embodiment, a medical imaging system is provided. The medical imaging system includes a base, a housing extending upwardly from the base and having opposed lateral sides, the housing being configured to support an operator console and display, a plurality of wheels supporting the base and providing mobility for the system, and a removable storage bin received in a recess in the housing. The storage bin is movable from a stowed position in which the storage bin is received within the recess and is generally contained within the housing, and an access position in which the storage bin extends from one of the lateral sides of the housing permitting access to contents of the storage bin by a user from a front of the system.

In yet another embodiment, a method of storing items on ultrasound imaging apparatus having a base, a housing extending upwardly form the base and supporting an operator console and display, and a plurality of wheels supporting the base is provided. The method includes the steps of inserting a storage bin into a recess in the housing and positioning the storage bin in a stowed position such that opposed sides of the storage bin are generally contiguous with opposed lateral sides of the housing. The storage bin is configured to slide bidirectionally from the stowed position at a right angle with respect to the lateral sides of the housing permitting access to contents of the storage bin by a user from a front of the apparatus.

DRAWINGS

The present invention will be better understood from reading the following description of non-limiting embodiments, with reference to the attached drawings, wherein below:

DETAILED DESCRIPTION

Figure 1:
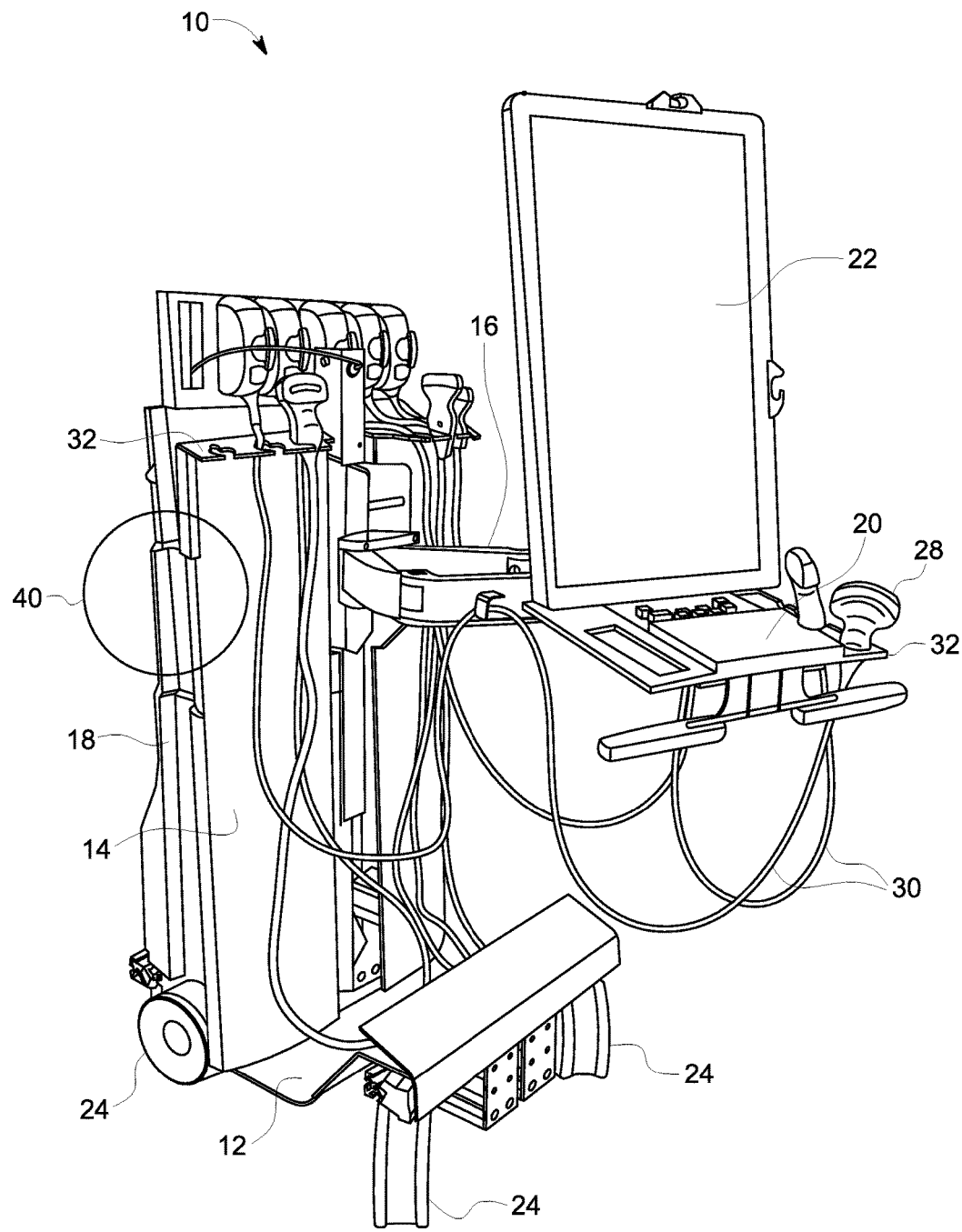
FIG. 1 is a perspective view of an ultrasound system incorporating a portable storage bin, according to an embodiment of the invention.

Reference will be made below in detail to exemplary embodiments of the invention, examples of which are illustrated in the accompanying drawings. Wherever possible, the same reference characters used throughout the drawings refer to the same or like parts. While embodiments of the invention are described in connection with a portable ultrasound imaging system, embodiments of the invention may also be applicable to other portable medical imaging systems and devices as well as wheeled carts, more generally.

As used herein, "operatively coupled" refers to a connection, which may be direct or indirect. The connection is not necessarily a mechanical attachment. As used herein, "bidirectionally" means in at least two directions.

Embodiments of the invention relate to an ultrasound or other medical imaging system and apparatus having a portable storage bin. In an embodiment, the system or apparatus includes a base, a housing extending upwardly from the base and having opposed lateral sides, a plurality of wheels supporting the base and providing mobility for the system, and a removable storage bin received in a recess in the housing. The storage bin is movable from a stowed position in which the storage bin is received within the recess and is generally contained within the housing, and an access position in which the storage bin extends from one of the lateral sides of the housing permitting access to contents of the storage bin by a user from a front of the system. In an embodiment, the storage bin is bidirectionally slidable in a manner such that the contents of the bin can be accessed from either side of the system.

Figure 2:
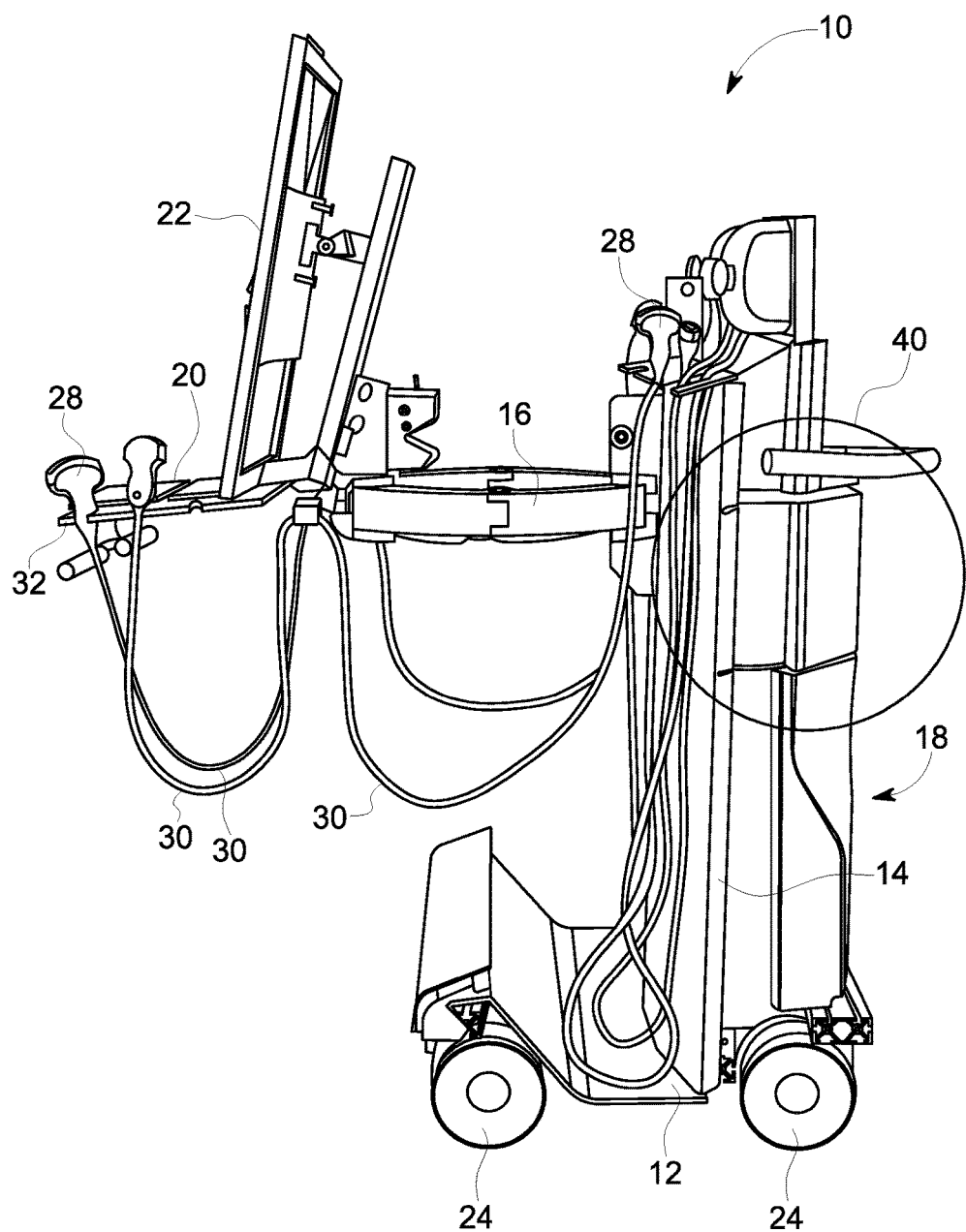
FIG. 2 is another perspective view of the ultrasound system of FIG. 1.

Referring to FIGS. 1 and 2, an ultrasound system 10 according to an embodiment of the invention is illustrated. As shown therein, the ultrasound system 10 includes a base 12, a frame 14 extending upwardly from the base 12, a support arm 16 extending outwardly from the frame 14, and a housing or totem 18 connected to the frame 14 opposite the support arm 16. In an embodiment, the support arm 16 is articulated and is configured to receive an operator console 20 and display monitor 22 on a distal portion thereof. As further shown in FIGS. 1 and 2, the ultrasound system 10 may include a plurality of wheels or casters 24 mounted to the base 12 that allow the system 10 to be easily moved from location to location.

In an embodiment, the housing or totem 18 on the rear of the system 10 may be formed from a plurality of stackable, plug-and-play type modules that serve a variety of functions, as discussed in detail hereinafter. In an embodiment, each of the modules may be removably mounted to the frame 14 via a pair of guide rails, although other fastening systems may also be utilized without departing from the broader aspects of the invention. In yet other embodiments, the modules may be fixedly attached to the frame 14 or integrally formed therewith.

Figure 3:
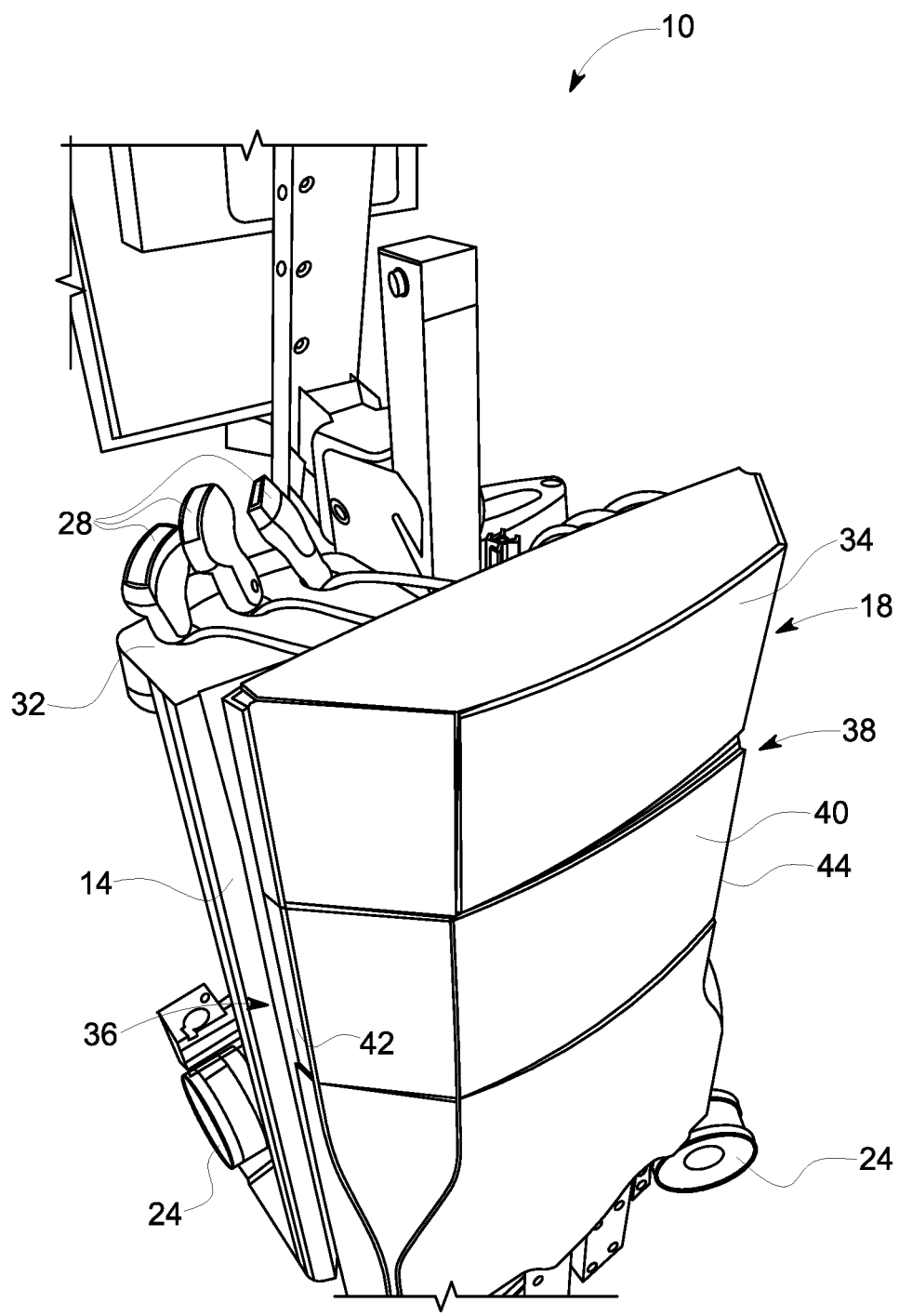
FIG. 3 is an enlarged, perspective view of a rear portion of the ultrasound system, illustrating the location of the portable storage bin.
Figure 4:
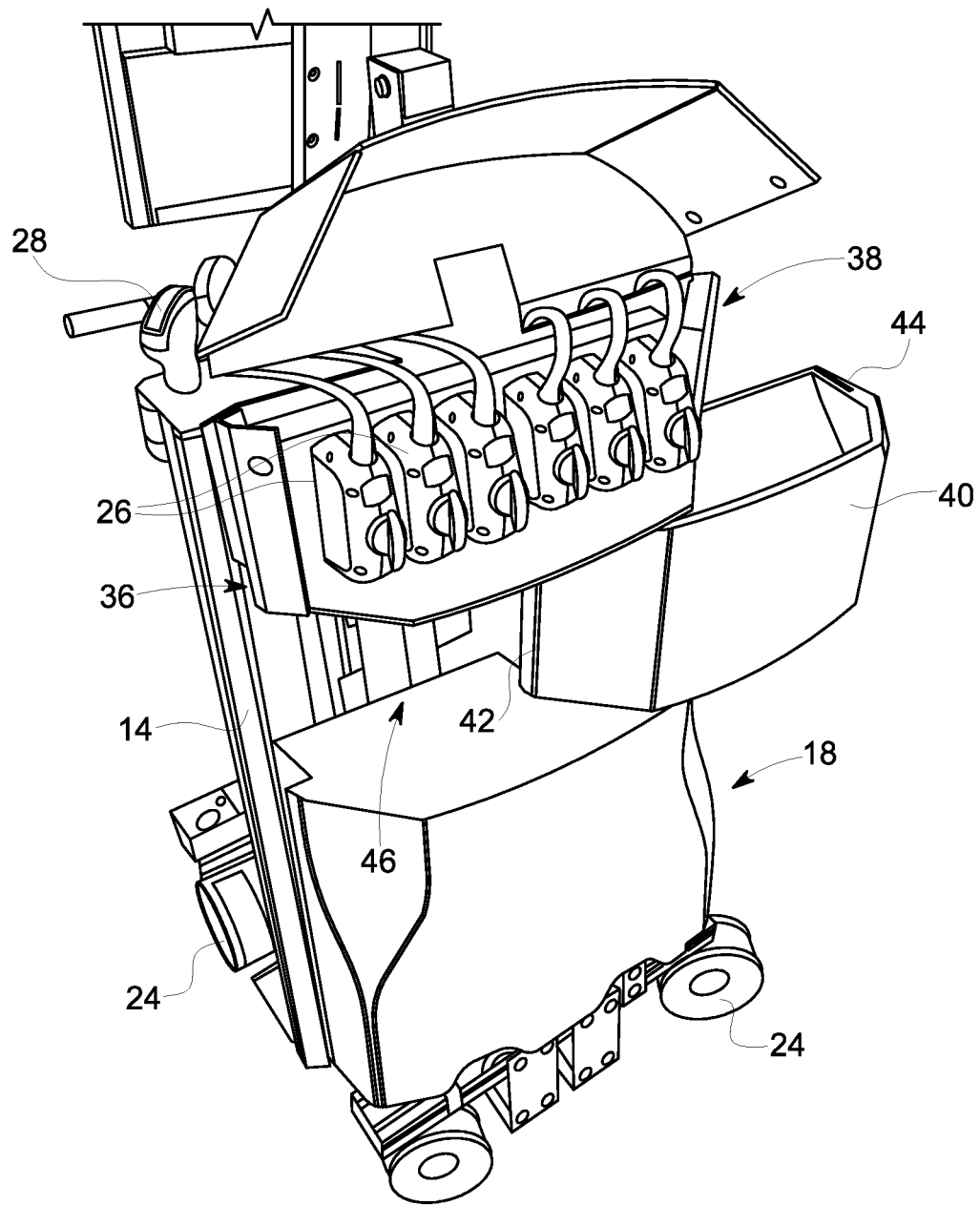
FIG. 4 is another enlarged, perspective view of the rear portion of the ultrasound system.

For example, with reference to FIGS. 3 and 4, a first module 34 may be an electronics module that may house a plurality of ports 26 for connecting a plurality of transducer probes 28 to signal processing subsystems located inside the housing 18 or other area of the system 10. Typically each probe 28 is designed to meet the requirements of a specific application and may be any type of probe known in the art. As shown in FIGS. 1-4, each transducer probe 28 is coupled to a respective port of the ultrasound imaging system 10 via a coaxial cable 30 and can be held in stowed position by a respective yoke 32. As best shown in FIGS. 1 and 2, the yokes 32 may be located on the frame 14 or be integrally formed as part of the operator console 20 for easy access by a technician or operator.

With specific reference to FIGS. 3 and 4, at least one of the modules may be a portable storage bin 40. In an embodiment, the portable storage bin 40 is positioned beneath the electronics module 34 in a recess 46 within the housing 18. The storage bin 40 is used to retain supplies or other devices needed to carry out the ultrasound imaging process on a patient, as discussed in detail hereinafter. As shown in FIG. 3, the storage bin 40 is in its center position, that is, the lateral sides 42, 44 of the storage bin 40 are generally contiguous to the lateral sides 36, 38 of the housing or totem 18 and thus, in that center position, the storage bin 40 is positioned directly beneath and generally in alignment with the module above and/or below it.

In an embodiment, the storage bin 40 is not affixed to the frame 14 or the modules above or below the storage bin 40, and is free to slide in any direction. In other embodiments, the storage bin may be slidably affixed to either the frame 14 or one or both of the modules above and/or below the storage bin 40. For example, the storage bin 40 may be slidably coupled to the frame 14 of the system 10 by means of conventional tracks, such as a roller tracks. A typical track may be similar to the use in conventional file drawers that have roller tracks and which enable the storage bin 40 to be movable bidirectionally from the center position in either direction at a right angle to the lateral sides 36, 38 of the housing 18.

With specific reference to FIG. 4, the storage bin 40 may be moved from its center position (shown in FIG. 3) such that one of its lateral sides is moved away from its contiguous position with respect to the corresponding lateral side of the housing 18. The storage bin 40 is able to slide in both directions from the center position, that is, bidirectionally (i.e., to the right and to the left in FIGS. 3 and 4), so that an operator or technician can access the contents of the storage bin 40 from either side of the system 10, and particularly when sitting or standing at the front of the system 10.

Thus, the system can be positioned on either side of a patient bed or adjacent to other equipment or obstructions without the bed or other obstructions inhibiting free access to the contents of the storage bin 40. The storage bin 40 can be easily accessed by simply sliding the bin 40 out of the housing 18 in a direction opposite the patient's bed or other obstruction next to which the system 10 is positioned.

Figure 5:
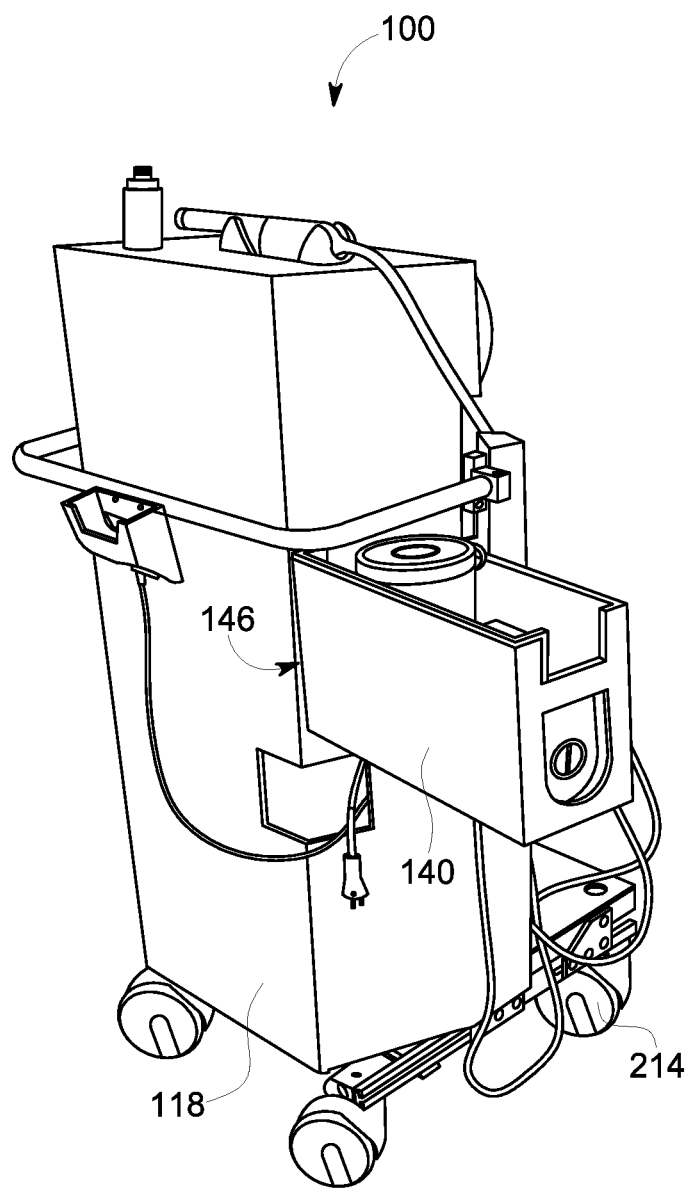
FIG. 5 is perspective view of an ultrasound system incorporating a portable storage bin, according to another embodiment of the invention.

Turning now to FIG. 5, an ultrasound system 100 having a bidirectional sliding storage bin 140 according to another embodiment of the invention is illustrated. The ultrasound system 100 is substantially similar to ultrasound system 10 and is mounted on wheels or casters 124 that provide portability. As with system 10, the portable storage bin 140 is slidably received in a recess 146 in the housing 118 on the rear portion of the system 100 such that the storage bin 140 may be pulled out from either side.

Figure 6:
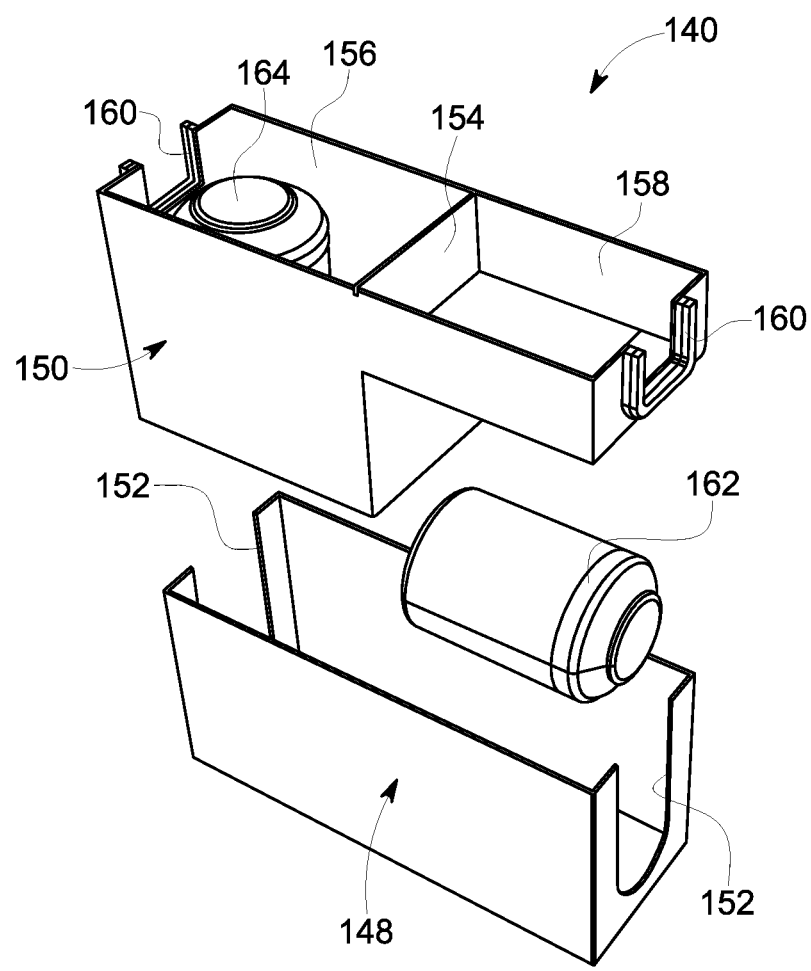
FIG. 6 is an exploded, perspective view of the portable storage bin for use with the ultrasound system of FIG. 1 or 5, according to an embodiment of the invention.
Figure 7:
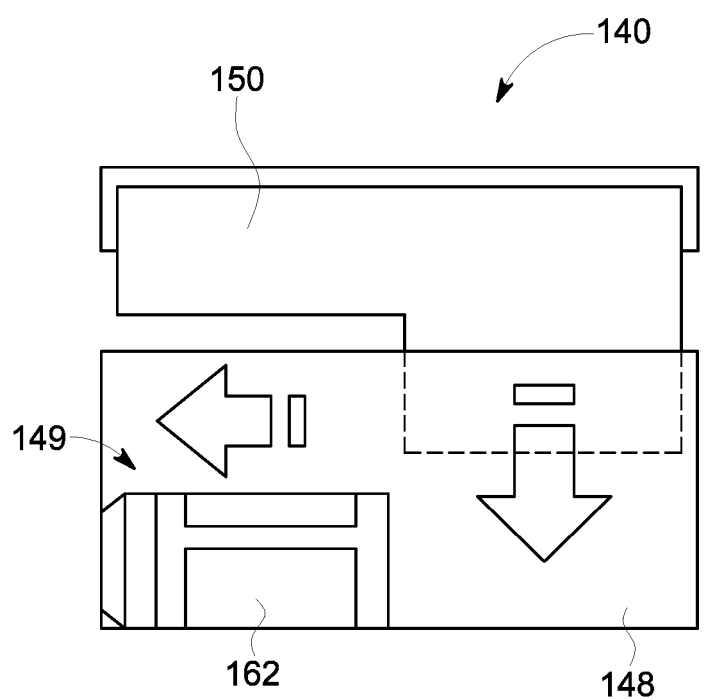
FIG. 7 is a side elevational view of the portable storage bin of FIG. 6.
Figure 8:
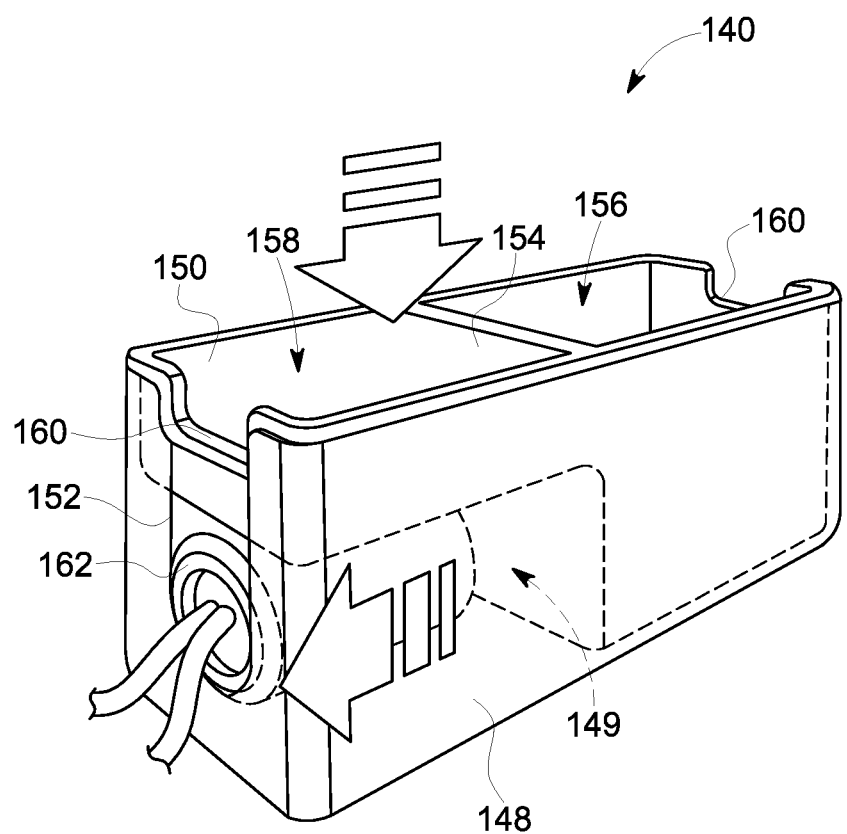
FIG. 8 is a perspective view of the portable storage bin of FIG. 6.

Referring to FIGS. 6-8, the configuration of the storage bin 140 is best illustrated. While FIGS. 6-8 illustrate storage bin 140, storage bin 40 of FIGS. 1-4 may be similarly constructed. In an embodiment, the storage bin 140 includes a first container 148 and a second container or insert 150 nestable with the first container 148. The first container 148 is generally rectangular in shape and has a pair of generally U-shaped, vertically extending slots 152 formed in opposed, lateral sides thereof. The insert 150 is generally L-shaped and is divided into two compartments by a central wall 154. In particular, as shown in FIG. 6, the wall 154 divides the insert 150 into a rear compartment 156 defining a deep bin that is substantially the same depth as the first container 148, and a forward compartment 158 defining a shallow tray. In an embodiment, both lateral sides of the insert 150 may be formed with slots 160, the purpose of which will be discussed hereinafter.

As shown in FIGS. 6-8, the configuration of the insert 150, when received by the first container 148, defines a recess 149 beneath the shallow tray 158 that is sized to accommodate a container 162 of wipes or other accessories and/or supplies. For example, as best shown in FIG. 8, the container 162 may be laid on its side so that the wipes may be pulled from the container 162 through one of the slots 152 in the side of the first container 148 without removing the first container 148 from the storage bin 140, and even without sliding the storage bin 140 out from the housing 118. Another container 164, such as one containing additional wipes, gel or the like can be housed within the rear portion 156 of the insert 150. The shallow tray 158 provides for easy reach of items contained therein.

In an embodiment, the first container 148 may be between about 17 to about 19 inches long, between about 5.5 to about 7.5 inches wide, and between about 8 to about 10 inches deep, and the insert 150 may be between about 16.5 to about 18.5 inches long, between about 5 to about 7 inches wide. The deep bin 156 may be between about 8 to about 10 inches deep, while the shallow tray 158 may be between about 2.5 to about 3.5 inches deep. In an embodiment, the first container 148 may be about 18 inches long, 5.5 inches wide, and 8.75 inches deep, and the insert 150 may be about 17.5 inches long, 5 inches wide, and have a deep storage bin 156 that is about 8.7 inches deep and a shallow tray 158 that is about 3 inches deep. With such a configuration, the recess 149 beneath the shallow tray 158 is about 8 inches long, 5.5 inches wide, and 7.75 inches tall.

In yet other embodiments, the insert 150 may be customized (in both size and configuration) according to any customer need, in dependence upon the particular items to be stored and which may be typically necessary for system operation. For example, different inserts may be utilized depending on the type of imaging that is typically performed (e.g., GI imaging, cardiac imaging, etc.). It is contemplated that the storage bin 140 may provide storage for cleaning wipes, probe gel, towels, biopsy kits, and other accessories required for examinations.

Regardless of the particular configuration of the insert 150, the insert 150 and first container 148 within which the insert 150 is received provide enough storage space to accommodate at least a majority of the supplies needed for mobile use (i.e., a sufficient quantity of needed to make rounds and use the system 10, 100 in another area of a multi-floor hospital remote from a supply room or similar mass-storage facility where bulk quantities of supplies are typically kept).

In use, multiple storage bins 40, 140 may be preloaded with supplies needed for system use and stored in a supply room or like facility. It is contemplated that each such bin may be marked or coded according to a particular type of imaging that may be performed (and which is stocked with accessories needed to carry out such type of imaging or a particular procedure(s)). Prior to use of the system 10, 100, the system 10, 100 may be wheeled adjacent to the supply room and a stocked bin 40, 140 may be taken from the supply room and inserted into the recess 46, 146 on the rear of the mobile system 10, 100. The system 10, 100 may then be wheeled to another area of the hospital, or to another floor, where ultrasound imagining on multiple patients may be performed. Once the supplies in the bin 40, 140 are exhausted, a technician or operator can simply slide the bin 40, 140 from either side of the housing 18, 118 and replace it with another bin from the supply room that is pre-stocked with the necessary accessories and supplies. This quick and easy 'plug and play' eliminates downtime and improves ultrasound system efficiency, as a whole.

Figure 9:
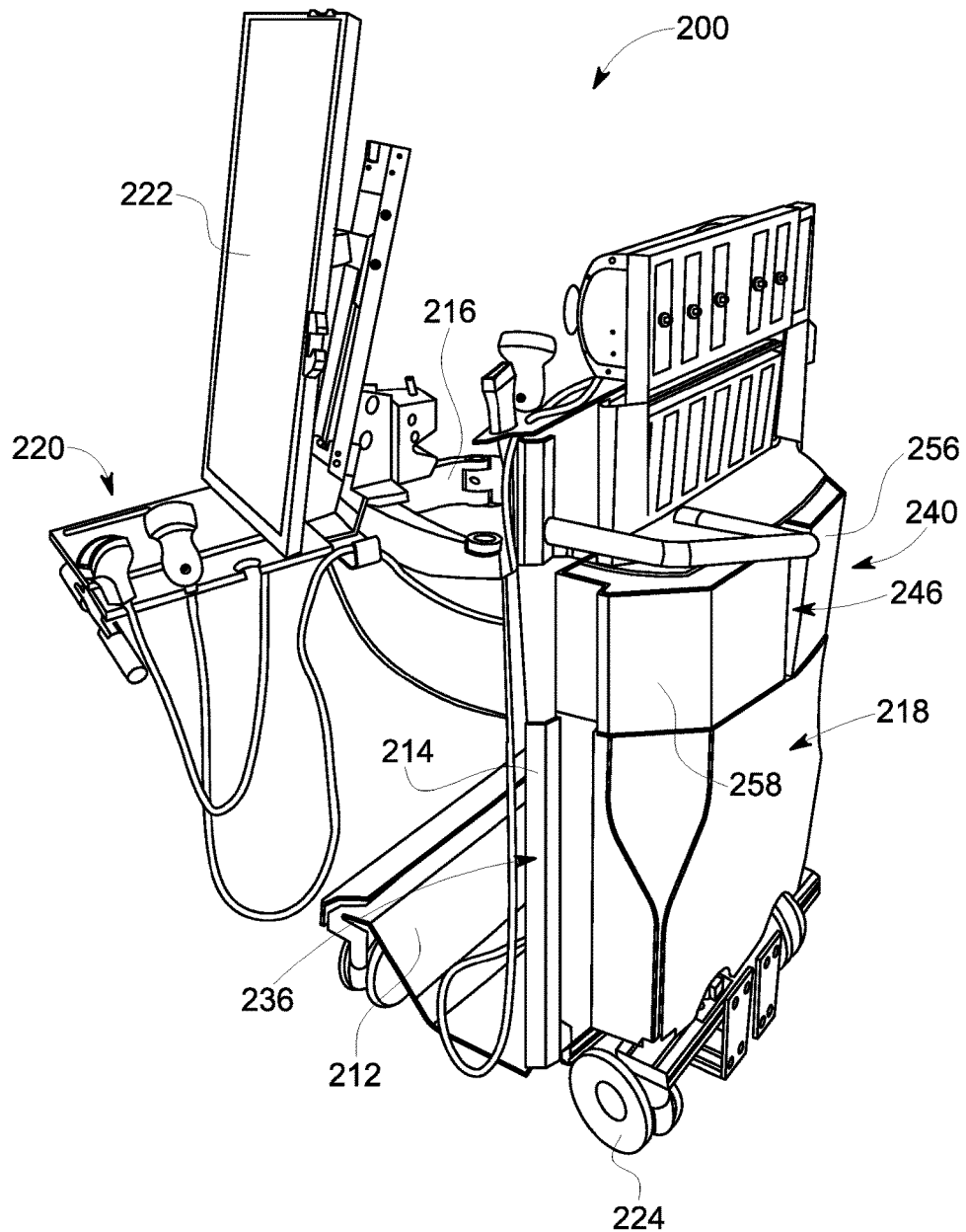
FIG. 9 is perspective view of an ultrasound system incorporating a portable storage bin, according to another embodiment of the invention.
Figure 10:
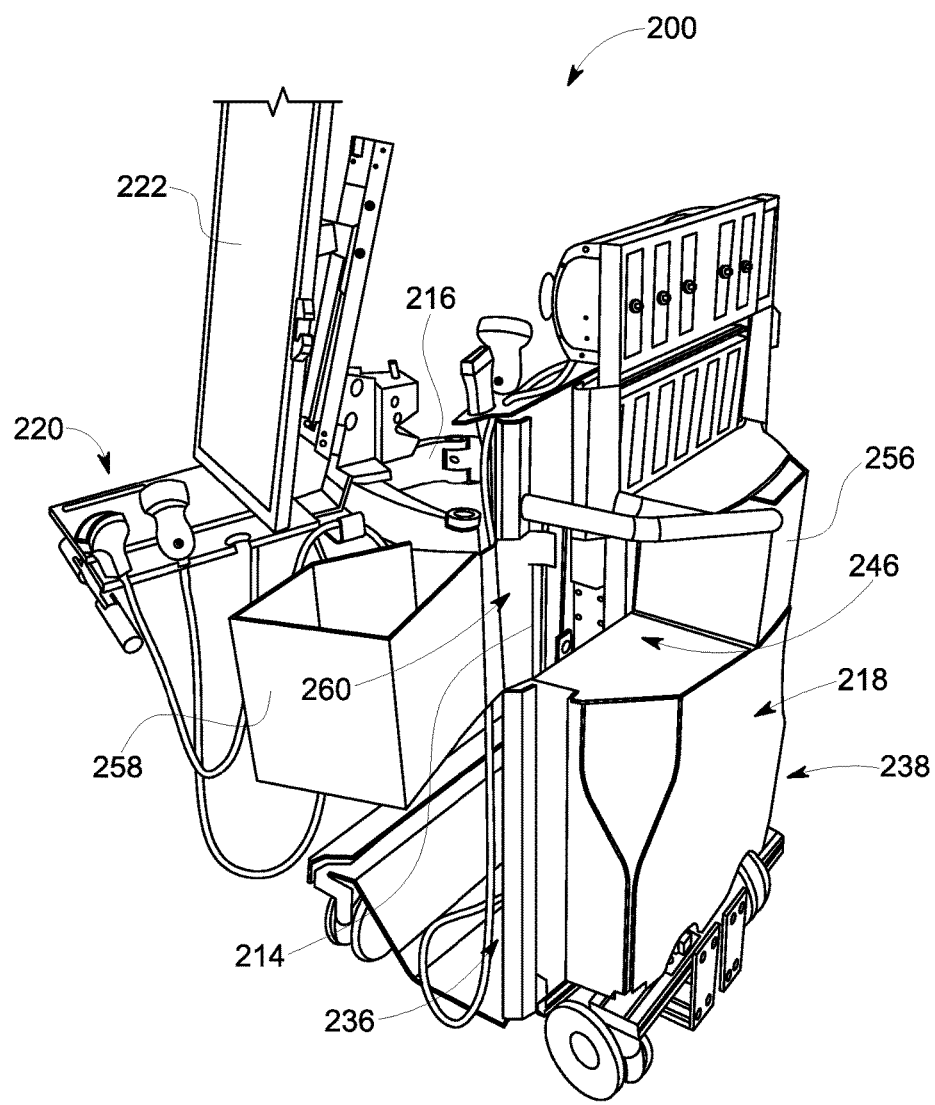
FIG. 10 is another perspective view of the ultrasound system of FIG. 9, showing operation of the portable storage bin.

Turning now to FIGS. 9 and 10, an ultrasound system 200 having a portable storage bin 240 according to yet another embodiment of the invention is illustrated. The ultrasound system 200 is substantially similar to ultrasound systems 10, 100 and is mounted on wheels or casters 224 that provide mobility. Like system 10, 100, the ultrasound system 200 includes a base 212, a frame 214 extending upwardly from the base 212, a support arm 216 extending outwardly from the frame 214, and a housing or totem 218 connected to the frame 214 opposite the support arm 216. The support arm 216 is articulated and is configured to receive an operator console 220 and display monitor 222 on a distal portion thereof, as discussed above.

As with systems 10, 100, the ultrasound system 200 may also include a portable storage bin 240 received in a recess 246 in the housing 218 on the rear portion of the system 200. Rather than being slidable within the recess 246, however, the storage bin 240 may be pivotally coupled to the system 200, as discussed hereinafter.

As illustrated in FIGS. 9 and 10, the portable storage bin 240 may have two independent compartments 256, 258 that are pivotally connected to the frame 214 of the apparatus 14, such as by a hinges 260 at opposed, lateral side edges 236, 238 of the housing 214. The compartments 256 are each pivotable about the respective hinges 260 so that they may rotate about a vertical axis from their stowed positions within recess 246 (shown in FIG. 9) towards the front of the system 200 where they are accessible to a technician standing or sitting at the front of the system 200 (as shown in FIG. 10). While FIGS. 9 and 10 illustrate independent compartments, 256, 258, it is contemplated that the portable storage bin 240 may be a single compartment that is rotatable about a single hinge on one side of the housing 218.

In an embodiment, the compartments 256, 258 may be selectively removable from the housing so that other pre-stocked compartments from a supply room or like storage facility may be quickly and easily connected to the system 200 for use. For example, in an embodiment, the hinges 260 may take the form of detents or a spring-biased rod connected to the portable storage bin 240 (or each of the compartments thereof), the ends of which are received in corresponding recesses formed in the housing 218 or the modules located above or below, enabling the bin 240 to rotate about the vertical hinge axis.

The ultrasound system incorporating the portable storage bin according to the invention therefore provides for quick and easy restocking of supplies when necessary, and obviates the need for piecemeal restocking of ultrasound accessories and supplies in various discrete recesses and other areas of the cart. In particular, the storage bin can be easily removed from the system for restocking and/or removed and replaced with a pre-stocked bin from supply. Additionally, the storage bin of the invention has a capacity large enough to accommodate substantially all of the supplies and accessories needed for an imaging procedure, enabling the system to be fully mobile and maintain complete functionality, regardless of where in a hospital or clinical setting the system is moved. In connection with the above, the ability to house the majority of accessories and/or supplies in a single area eliminates clutter in the operator's workspace, thus preventing the catching or tangling of probe cables on gel containers, wipes, etc., which is commonplace with existing systems that store gel containers adjacent to the operator console, while also ensuring that such items are kept close at hand and readily accessible to the operator from the front of the system.

Moreover, by providing a storage bin that can be opened to either side of the system, a technician or operator can position the system in almost any desired orientation in relation to a patient that is most convenient to carry out the imaging process, while not having to worry about whether access to needed supplies or accessories may be obstructed. For example, if one side of the mobile cart is positioned in close proximity to a patient's bed, the storage bin can simply be opened to the opposite side to permit access to its contents. In particular, the storage bin is easily accessible from either side of the system to a technician sitting or standing at the front of the system. In addition, as indicated above, a technician may even access certain supplies, such as cleaning wipes, through the slot in the side of the storage bin without having to open the bin. Similarly, the storage bin can be easily moved to its stowed position out of the way of an operator who may wish to stand or sit to the lateral sides of the system, allowing for unobstructed movement around the system.

Still further, the ability to accommodate different inserts within the main container of the portable storage bin allows the storage space to be customized according to a customer's specific needs, which may depend upon, for example, the particular type of imaging performed, the types of accessories and supplies utilized, and/or the specific packaging (shape and size) for the supplies.

In an embodiment, an ultrasound apparatus is provided. The ultrasound apparatus includes a base, a housing extending upwardly from the base and having opposed lateral sides, the housing being configured to support an operator console and display, and a storage bin received in a recess in the housing. The storage bin is movable from a first position in which the storage bin is received within the recess of the housing, and a second position in which the storage bin extends from one of the lateral sides of the housing. In an embodiment, the storage bin is removable from the apparatus. In an embodiment, the storage bin is configured to slide bidirectionally from the first position at a right angle with respect to the lateral sides of the housing. In an embodiment, the storage bin has sides that are generally contiguous to the lateral sides of the housing when the storage bin is in the first position. In an embodiment, the storage bin includes a first container and an insert nestable with the first container. In an embodiment, the first container includes a slot in at least one of the sides. In an embodiment, the insert is divided into at least two compartments, including at least a first compartment having a depth that is approximately equal to a depth of the first container, and at least a second compartment having a depth that is less than the depth of the first container. A floor of the second compartment is spaced from a floor of the first container and defines a recess therebetween, wherein the slot provides access to the recess from the side of the storage bin. In an embodiment, the storage bin is configured to rotate about a vertical hinge axis from a rear of the apparatus toward a front of the apparatus. In an embodiment, the storage bin includes a first compartment and a second compartment, each compartment being configured to rotate about a respective vertical hinge axis from the rear of the apparatus toward the front of the apparatus. In an embodiment, the apparatus includes a plurality of casters coupled to the base and providing mobility for the ultrasound apparatus. In an embodiment, the apparatus may include an articulated support arm extending from the housing and supporting the operator console and display. In an embodiment, the housing includes an electronics module containing a plurality of ports for connection of one or more transducer probes.

In another embodiment, a medical imaging system is provided. The medical imaging system includes a base, a housing extending upwardly from the base and having opposed lateral sides, the housing being configured to support an operator console and display, a plurality of wheels supporting the base and providing mobility for the system, and a removable storage bin received in a recess in the housing. The storage bin is movable from a stowed position in which the storage bin is received within the recess and is generally contained within the housing, and an access position in which the storage bin extends from one of the lateral sides of the housing permitting access to contents of the storage bin by a user from a front of the system. In an embodiment, the storage bin is configured to slide bidirectionally from the stowed position at a right angle with respect to the lateral sides of the housing. In an embodiment, the storage bin has sides that are generally contiguous to the lateral sides of the housing when the storage bin is in the stowed position. In an embodiment, the storage bin includes a slot formed in at least one of the sides of the storage bin, the slot permitting access to contents of the storage bin when the storage bin is in the stowed position. In an embodiment, the storage bin is configured to rotate about a vertical hinge axis from a rear of the apparatus toward the front of the apparatus. In an embodiment, the storage bin includes a first compartment and a second compartment, each compartment being configured to rotate about a respective vertical hinge axis from the rear of the apparatus toward the front of the apparatus.

In yet another embodiment, a method of storing items on ultrasound imaging apparatus having a base, a housing extending upwardly form the base and supporting an operator console and display, and a plurality of wheels supporting the base is provided. The method includes the steps of inserting a storage bin into a recess in the housing and positioning the storage bin in a stowed position such that opposed sides of the storage bin are generally contiguous with opposed lateral sides of the housing. The storage bin is configured to slide bidirectionally from the stowed position at a right angle with respect to the lateral sides of the housing permitting access to contents of the storage bin by a user from a front of the apparatus. In an embodiment, the method may also include the step of inserting an insert of the storage bin into a main container of the storage bin to form a customized storage arrangement.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasound apparatus, comprising:
   a base;
   a housing extending upwardly from the base and having
      a first lateral side and a second lateral side opposed to the first lateral side, the housing being configured to support an operator console and display;

a storage bin received in a recess in the housing, the storage bin having a first side and a second side that are generally contiguous to the first and the second lateral sides, respectively, when the storage bin is in a stowed position, the storage bin being bidirectionally slidable from the stowed position in both a first direction and a second direction each oriented along an axis normal to the first and the second lateral sides;

wherein the storage bin transitions to a first access position and a second access position when moved in the first direction and the second direction, respectively, the first and the second access positions both permitting access to contents of the storage bin.

2. The ultrasound apparatus of claim 1, wherein:
the storage bin is removable from the apparatus.

3. The ultrasound apparatus of claim 1, wherein:
the storage bin includes a first container and an insert nestable with the first container.

4. The ultrasound apparatus of claim 3, wherein:
the first container includes a slot in at least one of the sides.

5. The ultrasound apparatus of claim 4, wherein:
the insert is divided into at least two compartments, including at least a first compartment having a depth that is approximately equal to a depth of the first container, and at least a second compartment having a depth that is less than the depth of the first container;
wherein a floor of the second compartment is spaced from a floor of the first container and defines a recess therebetween; and
wherein the slot provides access to the recess from the side of the storage bin.

6. The ultrasound apparatus of claim 2, wherein:
the storage bin is configured to rotate about a vertical hinge axis from a rear of the apparatus toward a front of the apparatus.

7. The ultrasound apparatus of claim 2, wherein:
the storage bin includes a first compartment and a second compartment, each compartment being configured to rotate about a respective vertical hinge axis from a rear of the apparatus toward a front of the apparatus.

8. The ultrasound apparatus of claim 1, further comprising:
a plurality of casters coupled to the base and providing mobility for the ultrasound apparatus.

9. The ultrasound apparatus of claim 1, further comprising:
an articulated support arm extending from the housing and supporting the operator console and display.

10. The ultrasound apparatus of claim 1, wherein:
the housing includes an electronics module containing a plurality of ports for connection of one or more transducer probes.

11. A medical imaging system, comprising:
a base;
a housing extending upwardly from the base and having a first lateral side and a second lateral side opposed to the first lateral side, the housing being configured to support an operator console and display;
a plurality of wheels supporting the base and providing mobility for the system;
a removable storage bin received in a recess in the housing, the storage bin having a first side and a second side that are generally contiguous to the first and the second lateral sides of the housing, respectively, when the storage bin is in a stowed position, the storage bin being bidirectionally slidable from the stowed position in both a first direction and a second direction, each direction oriented along an axis normal to the first and the second lateral sides; and
wherein the storage bin transitions to a first access position and a second access position when moved in the first direction and the second direction, respectively, the first and the second access positions both permitting access to contents of the storage bin.

12. The medical imaging system of claim 11, wherein:
the storage bin includes a slot formed in at least one of the sides of the storage bin, the slot permitting access to contents of the storage bin when the storage bin is in the stowed position.

13. The medical imaging system of claim 11, wherein:
the storage bin is configured to rotate about a vertical hinge axis from a rear of the system toward a front of the system.

14. The medical imaging system of claim 11, wherein:
the storage bin includes a first compartment and a second compartment, each compartment being configured to rotate about a respective vertical hinge axis from a rear of the system toward a front of the system.

15. A method of storing items on an ultrasound imaging apparatus having a base, a housing extending upwardly from the base and supporting an operator console and display, and a plurality of wheels supporting the base, comprising the step of:
inserting a storage bin into a recess in the housing; and
positioning the storage bin in a stowed position such that opposed first and second sides of the storage bin are generally contiguous with opposed first and second lateral sides of the housing;
wherein the storage bin is configured to slide bidirectionally from the stowed position in both a first direction and a second direction each oriented along an axis normal to the first and the second lateral sides;
wherein the storage bin transitions to a first access position and a second access position when moved in the first direction and the second direction, respectively, the first and the second access positions both permitting access to contents of the storage bin.

16. The method according to claim 15, further comprising the step of:
inserting an insert of the storage bin into a main container of the storage bin to form a customized storage arrangement.

* * * * *